United States Patent [19]
Flores-Cotera et al.

[11] Patent Number: 5,660,977
[45] Date of Patent: Aug. 26, 1997

[54] FERMENTATION METHOD AND FERMENTOR

[75] Inventors: Luis Bernardo Flores-Cotera; Sergio Garcia-Salas, both of Mexico City, Mexico

[73] Assignee: Centro de Investigación y de Estudios Avanzados del Instituto Politécnico Nacional, Mexico City, Mexico

[21] Appl. No.: 529,410

[22] Filed: Sep. 18, 1995

Related U.S. Application Data

[60] Continuation-in-part of Ser. No. 429,687, Apr. 27, 1995, Pat. No. 5,593,890, which is a division of Ser. No. 963,980, Oct. 23, 1992, Pat. No. 5,426,024.

[51] Int. Cl.$^6$ .................................. C12Q 3/00; C12M 1/36
[52] U.S. Cl. .................. 435/3; 435/246; 435/259; 435/286.5; 435/286.6; 435/295.2; 435/301.1; 435/306.1; 435/812
[58] Field of Search .......................... 435/3, 41, 243, 435/246, 812, 818, 286.1, 286.5, 286.6, 289.1, 295.1, 295.2, 301.1, 259, 306.1; 95/1, 19, 24, 22, 154, 155, 23, 157, 241, 242; 96/155, 156, 157, 168, 169, 172, 174, 176; 261/121.1, 122.1, 126, DIG. 19

[56] References Cited

U.S. PATENT DOCUMENTS

| | | | |
|---|---|---|---|
| 3,563,858 | 2/1971 | Worthington et al. | 195/107 |
| 3,586,605 | 6/1971 | Hosler | 195/28 |
| 3,672,953 | 6/1972 | Coty et al. | 435/301.1 |
| 3,739,795 | 6/1973 | Hyde et al. | 55/178 |
| 3,806,423 | 4/1974 | Karrenbauer et al. | 195/109 |
| 3,857,757 | 12/1974 | Herrick et al. | 195/109 |
| 3,910,826 | 10/1975 | Kataoka | 195/142 |
| 3,926,737 | 12/1975 | Wilson et al. | 195/108 |
| 4,003,724 | 1/1977 | Payne et al. | 55/87 |
| 4,021,303 | 5/1977 | Nakabayashi | 195/5 |
| 4,169,010 | 9/1979 | Marwil | 435/247 |
| 4,263,143 | 4/1981 | Ebner et al. | 435/301.1 |
| 4,325,923 | 4/1982 | Botton et al. | 423/234 |
| 4,373,024 | 2/1983 | Hunt | 435/41 |
| 4,414,329 | 11/1983 | Wegner | 435/68 |
| 4,545,945 | 10/1985 | Prave et al. | 435/295.2 |
| 4,624,745 | 11/1986 | Sande et al. | 96/176 |
| 4,670,397 | 6/1987 | Wegner et al. | 435/289 |
| 4,752,564 | 6/1988 | Hopkins | 435/3 |
| 4,883,759 | 11/1989 | Hopkins | 435/289 |
| 4,987,082 | 1/1991 | Gallagher | 435/289 |
| 4,997,660 | 3/1991 | Wittler | 426/17 |
| 5,426,024 | 6/1995 | Flores-Cotera et al. | 435/812 |

FOREIGN PATENT DOCUMENTS 2172818  9/1986  United Kingdom.

OTHER PUBLICATIONS

Prins et al. Trends in Biotechnol. vol. 5, Nov. 1987.
Van't Riet et al. "Foam", Basic Bioreactor Design, Marcel Dekker, Inc., 1991, pp. 274–291.
Blenke, "Biochemical Loop Reactors", Biotechnology. vol. 2, H.J. Rehm and G. Reed Eds., VCH Verlagsgesellschaft, Weinheim, 1985, pp. 465–517.

*Primary Examiner*—William H. Beisner
*Attorney, Agent, or Firm*—Jacobson, Price, Holman & Stern, PLLC

[57] ABSTRACT

An improved method and fermentor for aerobic production of microbial cells and/or cell metabolites, having at least one ascending flow chambers and at least one descending flow chamber. The fermentor is especially useful in conducting high cell density fermentation processes which involves the controlled addition of an antifoam agent, for maintaining a predetermined and relatively high gas holdup within the fermentor or by release of the constituents of the microbial cells into the fermentor.

17 Claims, 4 Drawing Sheets

FERMENTATION METHOD AND FERMENTOR

CROSS REFERENCE TO RELATED APPLICATION

This application is a continuation in part of application Ser. No. 08/429,687 filed on Apr. 27, 1995, now U.S. Pat. No. 5,593,890, which is a divisional application of application Ser. No. 07/963,980 filed Oct. 23, 1992, now U.S. Pat. No. 5,426,024, both of which are incorporated herein by reference.

FIELD OF THE INVENTION

The present invention relates to a fermentation method and to an improved fermentor for growing microorganisms and/or producing metabolites from microorganisms, especially at high cell densities. Particularly, the fermentation method and the fermentor are suitable for conducting aerobic fermentation processes with controlled and relatively high gas holdup.

BACKGROUND OF THE INVENTION

So far, fermentations requiring an high rate of oxygen input, such as high cell density fermentation processes disclosed in U.S. Pat. No. 4,414,329 by Wegner, have been generally conducted in fermentors equipped with agitation means and mechanical foam breakers. The patent literature disclosing such fermentors includes: U.S. Pat. No. 4,670,397, U.S. Pat. No. 4,752,564, U.S. Pat. No. 4,883,759, U.S. Pat. No. 4,373,024. Agitated fermentors are adapted with difficulty for supplying the very high rate of oxygen input necessary to carry out high cell density fermentation processes in large scale plants. Several reasons, including the massive mechanical foam breakers required, made not commercially feasible to increase their size beyond certain limits. Stirrers and mechanical foam breakers used in high cell density fermentations require very high energy input, which is both costly and an operation and maintenance problem in large fermentors. Problems related to the mechanical design of drive shaft and bearings for transmitting the enormous torque arise. In addition, the seals associated with the stirrer and the foam breaker are often difficult to clean and sterilize; in many instances they create cleaning and asepsis problems. Consequently, there is a continuing need for improved fermentors of even larger capacity than those built to date, able of conducting aerobic fermentation processes at high cell densities. At the same time, fermentors which do not require moving parts for effective foam control, simple in construction, with low manufacturing cost and easy to maintain, together with high oxygen transfer rates at low power consumption, would provide sensible advantages. Fermentors with non mechanical foam control devices are very desirable. The advantages are: improved maintenance of sterility because no shaft is needed, construction of larger fermentors is possible because the design is not limited by the massive foam breaker required in large fermentors, lower initial cost and reduced maintenance. The present invention is intended to provide a fermentor and a fermentation method which overcome several shortcomings of fermentors and fermentation methods of the current technology. Particularly, this invention provides an improved fermentation method and a fermentor for carrying out fermentation processes with controlled gas holdup, while simultaneously preventing the formation of a foam layer by an hydrodynamic approach.

OBJECT OF THE INVENTION.

In one aspect, our invention relates to an improved fermentation method and apparatus for aerobic propagation of suitable microbial cells. In other aspect the present invention provides a fermentation method for conducting high cell density fermentation processes. Still another object of the present invention is to provide an improved fermentor, which is economical, efficient, simple and reliable for conducting high cell density fermentation processes. Further, the invention provides a fermentor suitable for conducting fermentation processes with controlled and relatively high gas holdup. Yet other object of the invention is to provide a fermentation method and a fermentor suitable for preventing the formation of a foam layer by an hydrodynamic approach.

The method of the present invention can be generally characterized as the aerobic fermentation of a suitable carbon source, assimilable by a microorganism, in a fermentor with controlled and relatively high gas holdup. A further distinctive characteristic of our method is that foaming is prevented through an hydrodynamic approach which does not require any mechanical device. The gas holdup can be defined as the volume fraction of gas phase (e.g. air) contained within a given volume of a mixture of gas and liquid phases, or as the ratio of volume of gas phase to the sum of volumes of gas and liquid phases. A distinction is made between gas holdup and foam: in gas holdup the gas bubbles dispersed in the liquid are more spherical and the gas/liquid volume ratio usually is lower than two; while the bubbles in the foam are polyhedral, forming a honeycomb structure, and the gas/liquid ratio is larger than two and usually larger than three. Still a more simple practical distinction can be made: gas holdup is the volume fraction of gas in the gassed broth and foam is a layer of polyhedral bubbles on top of the fermentation broth. The method of our invention can be used for controlling and maintaining a relatively high gas holdup in the gassed broth contained inside a fermentor, while simultaneously preventing the formation of a foam layer without assistance of mechanical devices. Fermentations Which demand very high oxygen transfer rates for microbial cell growth or cell metabolites production in a fermentation broth containing a carbon source can be enhanced by our invention.

SUMMARY OF THE INVENTION

Aerobic microbial conversions are oxidation reactions which demand large quantities of molecular oxygen. Hence, one of the main factors limiting the microorganisms generation rate is the oxygen transfer capacity in the fermentor. The oxygen transfer rate is primarily a function of bubble surface area, consequently, the oxygen containing gas is frequently introduced into fermentors in a fine bubble form, in order to provide a large contact surface area between the gas and liquid phases. Nevertheless, fine gas bubbles dispersed in pure liquids or in some fermentation broths, tend to join to form larger ones. So, even with the finest primary dispersion and depending on the degree of turbulence, bubble sizes between about 2 to 5 mm are formed after leaving the sparging zone. This phenomenon known as bubble coalescence, is caused by the fact that a liquid film between two adjacent gas bubbles becomes thinner and thinner until it eventually breaks down. Fermentation broths generally contain surface active materials derived from microbial activity. In some cases, for example when growing yeast on sugar cane molasses or a cellulolitic bacteria on sugar cane bagasse, coalescence is naturally suppressed with elapsed fermentation time, as surface active materials released from microorganisms accumulate in the fermentation broth. As a consequence, gas holdup generally increases with time and the fermentation broth develops a strong tendency of foaming. It is generally accepted, that an increasing-gas holdup trend and foam development are the result of stabilization of liquid films by proteins released from microorganisms. Foaming and gas holdup are thus strongly dependent on the properties of the broth. In other words, foaming and coalescence characteristics of the gassed broth are usually related. The gas holdup is a very important parameter in fermentation processes, because it determines the contact surface area between the gas and liquid phases. Consequently, it affects the oxygen transfer rate. A foaming broth can show better oxygen transfer characteristics, by a factor of two or more than a broth with coalescing characteristics. Since non coalescing characteristics increases the oxygen transfer rate, this effect is desirable, if suitable means to prevent foaming are provided. Excessive foaming is a common problem in many fermentation processes. Foaming results in inefficient use of fermentor volume and in an heterogeneous fluid with the bulk of cells trapped in the foam. Overflow can easily occur and exit filters wetted, resulting in an increasing contamination risk. In practice foam control has required a compromise between the positive effects on oxygen transfer and the negative effects of foaming.

Foaming is commonly reduced by sudden addition of antifoam agents in response to the level of the foam. This, however, causes considerable reduction in gas holdup and oxygen transfer rate because collapse of the foam also favors increased bubble coalescence in the liquid phase. Such an effect results in severe oxygen debt and reduced yields. Steady state conditions are lost during a continuous fermentation process as a result of these disturbances and furthermore the broth volume varies uncontrollably with variations in gas holdup.

According to one aspect of the invention, a method and fermentor are employed to maintain a predetermined and relatively high gas holdup within the fermentor vessel, by continuously controlling the antifoam feed rate in response to gas holdup in the gassed broth. Furthermore, to prevent foam accumulation within the upper part of the fermentor vessel without the use of mechanical devices, while maintaining a relatively high oxygen transfer rate.

Our fermentor is provided with gas holdup sensing means to provide a continuous output signal responsive to the gas holdup in the gassed broth contained in the fermentor. The fermentor is also provided with a controller operatively related to said gas holdup sensing means, to regulate or alternately activate/deactivate antifoam addition in response to said gas holdup sensing means.

Coalescence is strongly impeded during a fermentation process by extracellular materials naturally released from microorganisms. Since smaller gas bubbles are formed, and maintained, more bubbles are entrained into the downflow, and the gas holdup is greater than desired, the antifoam flow rate shall be increased through the control action to cause an increased rate of bubble coalescence and by this means slowly reduce the gas holdup to desired values. If the gas holdup is lower than desired, the antifoam feeding shall be reduced or even stopped through the control action to prevent a further gas holdup fall. In other fermentation processes, particularly some using synthetic carbon sources such as methanol or ethanol, bubble coalescence is not naturally hindered in a suitable degree to allow for the high oxygen transfer rates necessary to conduct a high cell density fermentation process. In these cases, high gas holdup and suitable oxygen transfer rate can be still achieved, by hindering bubble coalescence within the broth, through artificially provoking the release of surface active materials from microorganisms. This can be achieved, by mechanically, thermally or chemically disrupting the membranes of a portion of the microorganisms in the fermentor, so as to release or cause the release of the constituents of the said disrupted microorganisms. The microorganisms membranes can be disrupted by different means such as the exposure of the microorganisms to high temperature, high pH or low pH. The membranes of the microorganisms can be ruptured or disrupted by exposing the microorganisms to high frequency vibration and mechanical shearing, to chemicals normally fed to the fermentation process or pH control chemicals. The release of the constituents of the microorganisms according to our method is carried out in response to the gas holdup detected in the gassed broth contained inside the fermentor. By suitably treating a portion of the microorganisms, a fermentation broth with suitable non coalescing characteristics can be produced. At the same time, our fermentation method can be used to prevent the occurrence of foaming in the resultant non coalescing fermentation broth through an hydrodynamic approach, to produce a fermentation broth with high oxygen transfer characteristics but without foaming. Our invention can be used to enhance known fermentors for aerobic culturing of microorganisms, preferably but not exclusively the loop fermentors described by Blenke in H. J. Rehm and G. Reed (Ed.) "Biotechnology" volume 2, chapter 21, pp. 470–479, VHC Verlagsgesellschaft, Weinheim (1985). Non stirred loop fermentors are preferred, but our invention can also be used with stirred loop fermentors such as those described in U.S. Pat. No. 4,883,759, to avoid the use of costly mechanical foam breaker devices. Suitable, fermentors include but are not restricted to loop fermentors, fitted with internal guiding means forming at least a chamber of ascending flow (riser) and at least a chamber of descending flow (downcomer), communicating with each other at their upper and lower ends, to permit broth circulation in a loop pattern. An oxygen containing gas is injected near the lower end into the riser, this simultaneously serves to aerate the broth and to cause it to circulate upwardly in the riser and downwardly in the downcomer. The oxygen containing gas may be supplied by any suitable means. Conveniently, the gas is supplied into the riser through a pipe with plurality of holes. Said gas can also be sparged through venturi type nozzles, porous media or open ended pipes, if desired with associated downstream bubble breakers such as meshes, grids, vanes or moving parts, or any combination of these techniques known in the art. In addition to the airlift effect, any other mechanical or hydraulic means like impellers or liquid jets, can be used to promote turbulence or circulation of the broth or both. Our fermentor is fitted with gas holdup sensing means, to provide a continuous output signal responsive to the gas holdup in the gassed broth contained in the same. The fermentor is also equipped with a controller operatively related to said gas holdup sensing means, to activate/deactivate suitable means for releasing of the constituents of the microbial cells into the fermentor, in response to the sensed gas holdup. Coalescence is strongly impeded by activating the means for releasing of the constituents of the microorganisms. As coalescence is inhibited, gas bubbles become smaller and gas holdup becomes larger with time. It is important that gas holdup does not exceed a certain maximum value as this adversely affect mixing performance and fermentor volume utilization. If the gas holdup becomes greater than a predetermined maximum value, the release of the constituents of the microorganisms should be stopped to maintain or increase the rate of bubble coalescence and thus maintain or slowly reduce the gas holdup to suitable values. By alternately activating/deactivating the means for releasing of microorganisms constituents, gas holdup can be maintained at nearly constant and suitable values. A fermentation broth with inhibited bubble coalescence will easily produce a foam layer. Foam originates when bubbles ascending in the riser reach the free surface within the fermentor. At the moment that the gas and liquid leave the bulk liquid volume, a process of drainage starts. This in turn induces a decrease in liquid content with a decreased distance between the bubbles, until mainly liquid films are present among them. This phenomena can be appreciated as whitish spots of foam in "statu nascendi" leaving the riser. If the spots of foam in "statu nascendi" remain on the free surface, a honeycomb structure of bubbles separated by very thin walls of liquid connected by plateau borders, finally result. While running our loop fermentors, however, we have observed that at certain gassed broth levels, a characteristic liquid-flow pattern develops, such that the foam in "statu nascendi" is effectively entrained into the downcomer, through a vortex induced by the liquid flow deflection from the riser into the downcomer. If the vortex is maintained, the foam in "statu nascendi" cannot remain on the free surface, and the undesirable stable honeycomb structure of foam cannot be developed. In other words, if a vortex is induced by maintaining a suitable gassed broth level in the fermentor, the formation of a foam layer is not possible. By sustaining a suitable gassed broth level, while activating the means for releasing of constituents of the microorganisms or while controlling the addition of an antifoam agent, the gas holdup and the oxygen transfer rate can be increased without the accumulation of a foam layer at the top of the fermentor. There must be a free surface in the upper portion of the fermentor, the bigger air bubbles rise to this free surface and air is then disengaged from the broth without the use of any mechanical assistance. However, we should recognize that a vortex is not induced at too high gassed broth levels above the upper edge of the guiding means. Gassed broth levels higher than twice the diameter of the fermentor head (D) above the upper edge of the guiding means, generally result in a relatively flat free surface where spots of foam in "statu nascendi" remain to develop a foam layer, even before that gas holdup increases up to suitable values. Because of this reason, the gassed broth level should be preferably maintained between 0.1 and 2.0 D, and more preferably between 0.5 and 0.8 D, above the upper edge of the draft tube, in order to prevent the formation of a foam layer. Our controlled gas holdup fermentation method can be used preferably with continuous fermentors to achieve stable operating conditions and high oxygen transfer rates. In contrast with methods using mechanical defoamers, our fermentation method takes advantage of hydrodynamic foam suppression, which requires no shaft arrangements, facilitates keeping sterile conditions, requires no additional energy input, and is not a factor limiting fermentor scale up. The fermentation method and fermentor of our invention can be suitably used in many fermentation processes, wherein a carbon source is converted to microorganisms or their metabolites, and wherein an high oxygen transfer rate in a fermentation broth is required. Suitable sources of carbon material include any feed which can be used to grow microorganisms or produce their metabolites. For example, methanol, ethanol or any other carbon material which naturally give a fermentation broth with less than optimum non coalescing characteristics can be used. If bubble coalescence is naturally inhibited in a suitable degree or not, depends on several factors including microorganism characteristics, culture media composition and culture conditions. As required, detailed embodiments of the present invention are disclosed herein, however it is to be understood that the disclosed embodiments are merely examples of the invention which may be embodied in various forms. Therefore, specific structural and functional details disclosed herein are not to be interpreted as limiting, but merely as a basis for the claims and as a basis for teaching one skilled in the art to use the present invention in any appropriate. For convenience the detailed description will refer to a fermentation method and to a fermentor. It should be understood however, that the method and apparatus of the invention my be used in other processes wherein a gas is injected into a liquid, the resulting mixture is circulated, and in which disengagement of gas from the liquid takes place.

DETAILED DESCRIPTION OF THE INVENTION

Figure 1:
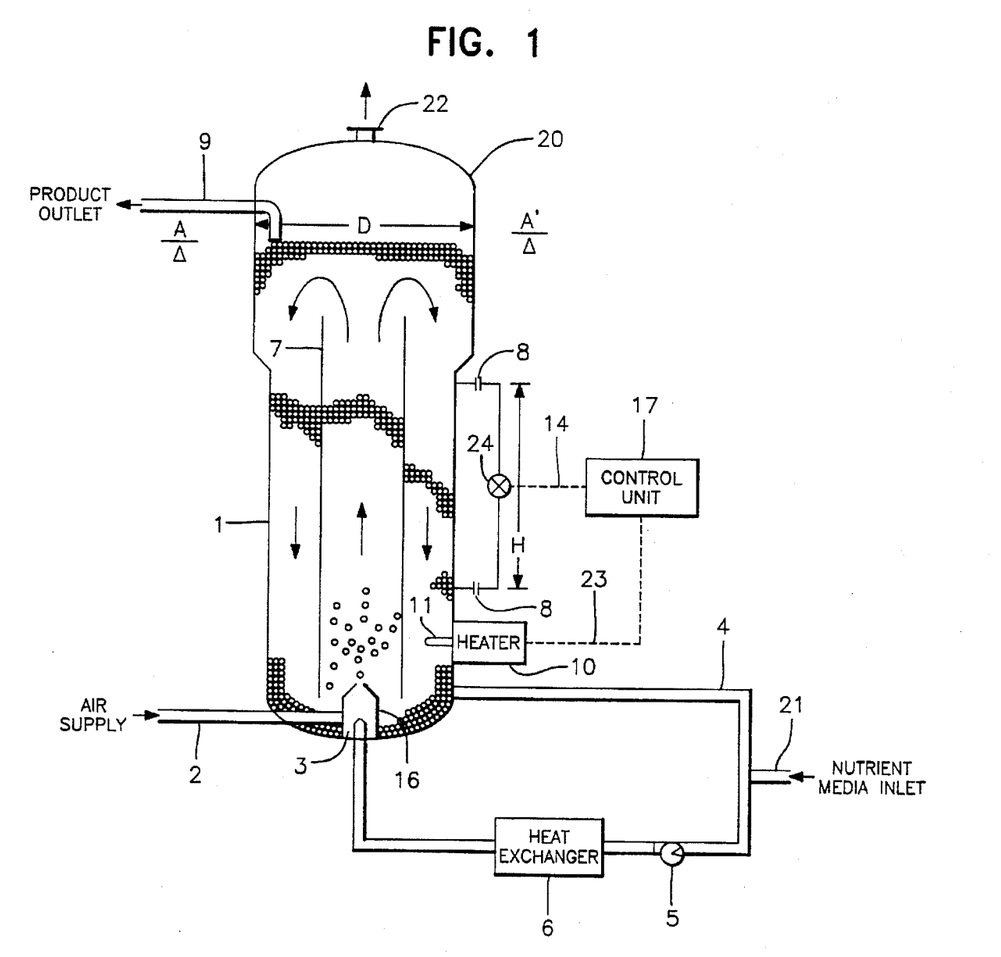
FIG. 1 is a side elevation of a fermentor illustrating one embodiment of the present invention.

FIG. 1 illustrates a fermentor generally designed by the reference character 20. The fermentor comprises a closed fermentor vessel 1 having a cylindrical upper section or fermentor head with an internal diameter denoted as D. The vessel 1 is provided with guiding means, in this case a draft tube 7, which provides a flow path for circulating the gassed broth contained within the vessel 1. Pipe 2, provides means for introducing a source of oxygen, such as air or air supplemented with pure oxygen, into the vessel 1. Air dispersion is accomplished by removing fermentation broth from the fermentor vessel 1, by means of a suitable pump 5, end reinjecting the broth through one or several Venturi jet mixers 3, whereby the broth is mixed with the air under high shear conditions to produce a dispersion of small gas bubbles in the broth. An outlet 22 communicates with the interior of the upper portion of the vessel 1 and provides means for exhausting the air from the vessel 1. The fermentor may include a heat exchanger 6, which serves as a cooler to prevent the temperature of the circulating culture from rising above the optimum temperature of growth of the microorganism. One or several inlets 21, provide means for delivery of a nutrient medium containing suitable sources of carbon, nitrogen, phosphorus, potassium, magnesium, calcium, sulfur, as well as trace quantities Of copper, manganese, molybdenum, zinc, iron, boron, iodide, selenium and any other nutrient that the fermentation process could require. The relative quantities of these nutrient materials can vary in accordance with the microorganism used or with the metabolite being produced. Nutrient medium may also contain vitamins if their presence is required for microorganisms growth, precursor compounds of the metabolite to be produced or the required chemical compounds for biochemical conversions. The fermentor vessel 1, is provided with means for sensing the gas holdup in the circulating broth. FIG. 1 illustrates, a fermentor vessel 1 provided with sensing means 8, for sensing the differential pressure between two sensing points separated a vertical distance H, in contact both with the gassed broth. The sensed differential pressure is derived from the hydrostatic-pressure difference of the broth between the sensors 8, and is indicative of the gas holdup in the zone between such sensors. The differential pressure (dp) measured as column of liquid, given in centimeters (cm), is related to gas holdup ($\epsilon$) by equation: $\epsilon=1-dp/H$, where H is given in cm. The sensing points 8 can be located in the downcomer or in the riser regions, or in any other suitable region of the fermentor because gas holdup in different regions are close related. Any suitable differential pressure sensing device which provides a suitable signal output in response to the differential pressure can be used. Preferred sensing devices are those used for pressure measurements in sanitary applications, featuring stainless steel seal diaphragms and isolated electrodes, forming a variable capacitor. Pressure applied to pressure sensors 8, causes a slight deflection of diaphragms, which in turn changes the capacitance. This capacitance is detected and converted to a highly accurate signal by transmitter 24. This signal is proportional to the sensed differential pressure. The output signal from the transmitter 24, is transmitted by a suitable conduit 14 to a control unit 17. If bubble coalescence is not naturally impeded in a suitable degree, an output signal 23 from the control unit 17 in response to the thus sensed gas holdup will cause the activation of heater 10, and the resulting heating of the heating element 11. Microorganisms coming in contact with or in close proximity to the heating element 11 will be killed and disrupted, and their constituents released to the broth, which in turn will hinder bubble coalescence causing an increase of gas holdup. It is important that gas holdup does not exceed a certain maximum value as this will adversely affect the circulation rate, bulk mixing and volume utilization. After a time-period of activation of heater 10, the sensed gas holdup eventually becomes higher than this maximum value. The output signal 23, from the control unit 17, in response to the sensed gas holdup, will cause the heater to turn off, thus deactivating the heater element 11 and causing the cessation of disrupting the membranes of microorganisms thereby within the fermentor vessel 1. By alternately activating/deactivating the heater 10, the gas holdup can be maintained at suitable and near constant values. It has been described an on/off gas holdup control, however other well known strategies in the art such as proportional, integral, derivative or a combination of them, can be also used to activate/deactivate the heater 10 for killing of microorganisms in response to the sensed gas holdup. After activation of heater 10, bubble coalescence is inhibited. Besides the gas holdup increasing trend, the fermentation broth develops a strong tendency of foaming. By maintaining a suitable gassed broth level within the fermentor vessel 1 for inducing a ring vortex as an outcome of the broth flow deflection from the draft tube into the annular space, foaming is effectively prevented. Foam in "statu nascendi" is effectively entrained through the vortex into the downcomer, thus preventing the development of a foam layer. The simplest way to maintain a desired gassed broth level, is fitting the vessel 1 with one or more overflow pipes 9, which provide means for drawing off a portion of the broth, to maintain the gassed broth level at near the line A-A' in FIG. 1. Alternatively, a wide variety of level measuring instruments can be used, for sensing the interface between the gassed broth and gas phase and provide a suitable signal output for automatically controlling the gassed broth level. Suitable sensing devices may include but are not restricted to conductive, capacitive, ultrasonic, displacer, and float transmitters. As previously described, gas holdup can be preferably sensed through measuring the pressure difference between two points separated a known vertical distance. Additionally, other methods can be used for gas holdup sensing. Accurate measurements of gas holdup can be made by measuring the difference in the refractive index between the gas and liquid. The technique requires the use of glass fibers and opto-electronic couplings normally used in telecommunication. Radiation absorption is another possibility. The method is based on the principle that liquids absorb the radiation much better than gases. Other method involves measuring the electric conductivity of the two phase dispersion, but this method is difficult to use with fermentation broths, because the electric conductivity depends not only on the gas fraction, but also on the concentration of salts which may change with time. Another method requires a standard hot-film anemometer probe, based on measuring the difference of heat conductivity between the liquid phase and the gas phase. Gas holdup can also be measured as the fraction of time that a given sensor point is in the gas phase in relation to the total time. The use of such type of sensor is rather complicated to date and is not commercially available.

Figure 2:
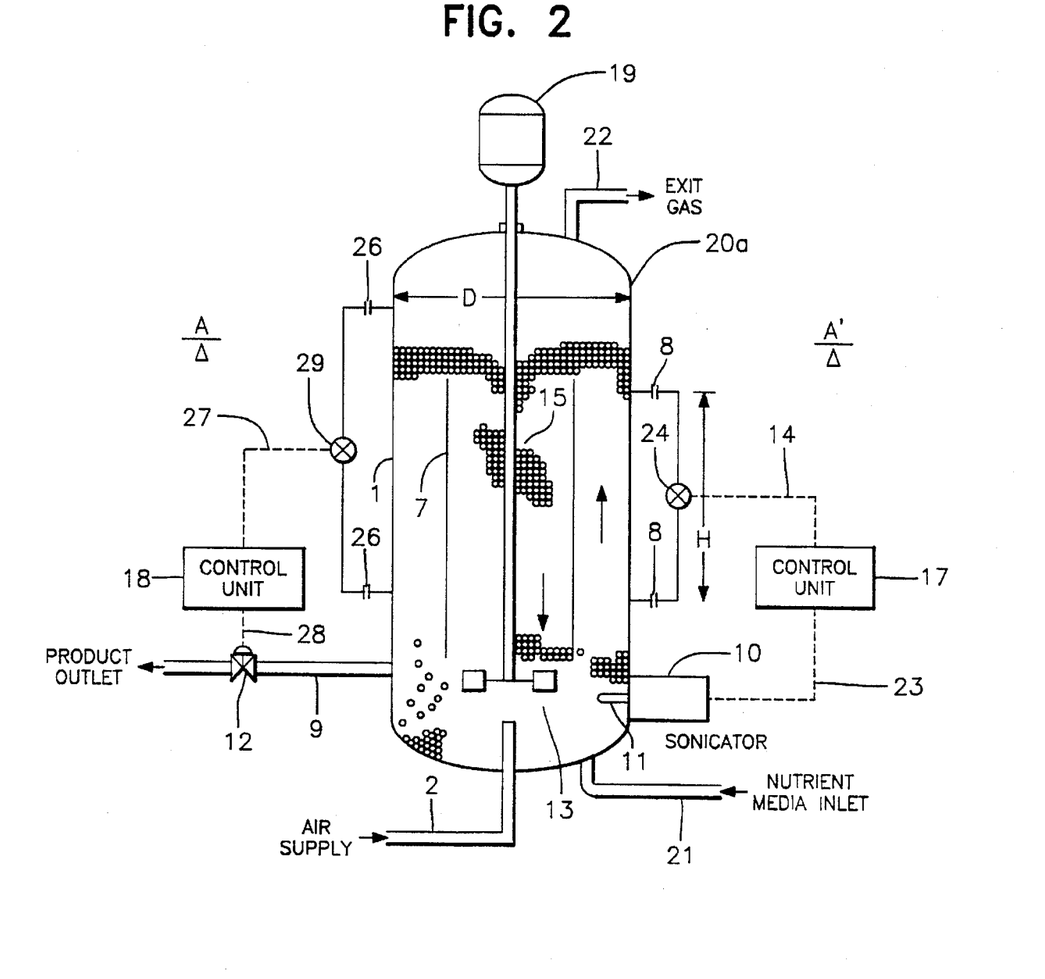
FIG. 2 is a side elevation of a second embodiment of the fermentor according to the invention.

In the fermentor described in the preceding paragraphs, the riser occupies the central region of the fermentor and the downcomer section surrounds it. It is equally possible and preferred in some cases, that the downcomer section should be in the center and the riser should form an annuli around it. Many other geometrical arrangements are possible, coaxial and symmetrical arrangements are preferred, however non coaxial and non symmetrical are also feasible. FIG. 2 illustrates another form of fermentation apparatus 20a, which is a modified version to of the apparatus 20. The elements of the apparatus 20a having the same function that in the previously described apparatus 20, are identified by the same reference numerals. The apparatus 20a differs from the apparatus 20 in the following aspects: Apparatus 20a is equipped with an agitation system having a turbine impeller 13, a shaft 15, and a driver 19. In apparatus 20a, the air dispersion is achieved by the rotating turbine impeller 13.

Instead of an heater 10 in apparatus 20, apparatus 20a includes a sonicator 10, operatively connected to a control unit 17. In operation of apparatus 20a, the control unit 17 activates sonicator 10 in response to the output signal from the transmitter 24. The sonication probe 11 thus transmits vibrations to the broth enclosed within the vessel 1, of sufficient intensity to rupture the membranes of a portion of the microorganisms which come in contact or in close proximity with the sonication probe 11. The constituents of the ruptured microorganisms are thus released to the broth thereby inducing enhancement of gas holdup. Like in fermentor 20, the cessation of disrupting the membranes of the microorganisms in the fermentor 20a takes place in response to a predetermined maximum gas holdup. By alternately activating/deactivating the sonicator 10, the gas holdup can be maintained at suitable and near constant values.

In apparatus 20a accumulation of foam within the upper end portion of the vessel 1 is prevented by controlling the broth level in the fermentor, thereby providing a broth flow path such that foam in "statu nascendi" is effectively entrained into the downcomer through a central vortex induced by the broth flow deflection from the annular space into the draft tube. Apparatus 20a, is fitted with a liquid level control system, which under controlled gas holdup conditions, provide means for measurement and control of the gassed broth level. The liquid level control system-comprises the following: a differential pressure sensing device 26, a transmitter 29, a control unit 18 and suitable means for withdrawing the broth, in this case, a valve 12. The differential pressure sensing device 26, has a bottom pressure sensor suitably located to be in contact with the gassed broth, and a top sensor suitably located to be in contact only with the gas phase. The control unit 18, provides an actuating signal 28 to adjust the valve 12, which provides means to regulate the drawing off of broth, in response to the differential pressure signal transmitted via conduit 27, to said control unit 18.

Figure 3:
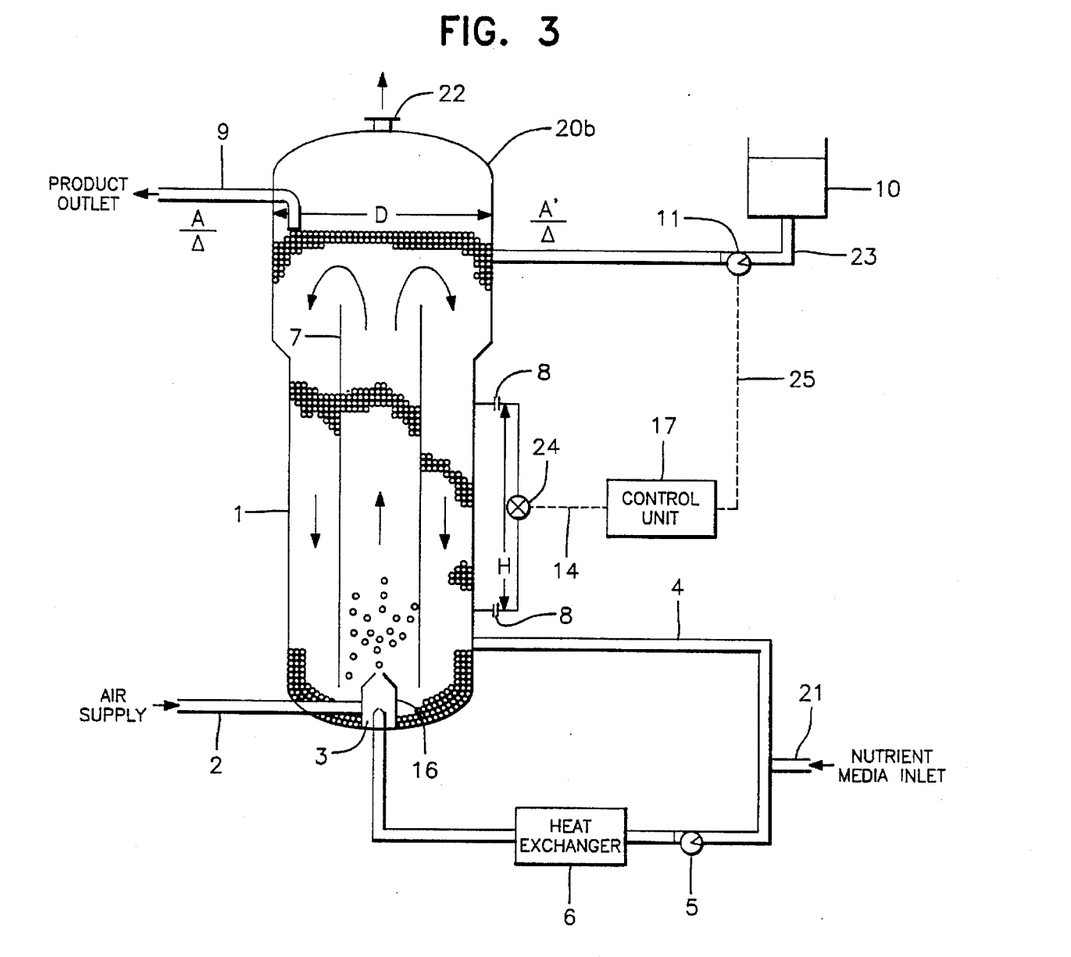
FIG. 3 is a side elevation of a third embodiment of the present invention.

FIG. 3 illustrates another form of fermentation apparatus 20b. The elements of the apparatus 20b have the same functions as those similarly described above in apparatus 20 and identified by the same reference numerals. Apparatus 20b differs in the following aspects:

Apparatus 20b, instead of having a heater 10, as in FIG. 1, an output signal 25 from the control unit 17, in response to the sensed differential pressure, provides an activating signal to adjust the flow rate of antifoam agent from supply 10 delivered to the fermentor, through tube 23, by pump 11 from an antifoam container 10.

Many chemical compounds can be used as antifoam agents, these include but are not limited to esters, alcohols, siloxanes, silicones, sulfites, sulfonates, fatty acids and their derivatives. Different control strategies, including proportional, integral, derivatives or a combination of them, can be employed to adjust the antifoam agent flow rate in response to the sensed differential pressure. The antifoam agent addition causes an increased rate of coalescence of air bubbles, and consequently a reduction of gas holdup in the gassed broth contained inside the vessel 1. If the gas holdup becomes lower than desired, the antifoam agent flow rate shall be reduced or even stopped through the control action to prevent a further drop of the gas holdup. On the other hand, if the gas holdup becomes higher than desired, the antifoam agent flow rate shall be increased through the control action in order to reduce gradually the gas holdup to the desired values. The controller also can be an on-off type with time delay to prevent overcharging of antifoam. In such a case, if the gas holdup is higher than desired, the antifoam added in response to the control signal 25 will increase the coalescence of the air bubbles, and consequently it will cause a reduction of gas holdup in the vessel 1. If the gas holdup is still higher than the set point after a determined amount of time (for example 3 minutes) from pump 11 activation, a new control action can be allowed. This control action shall be taken as many times as required at predetermined time intervals, while gas holdup remains higher than desired. The amount of antifoam agent added with each control action in this case is very critical, since relatively large amounts of addition, will cause undesirable steep gas holdup reduction and consequently a sharp oxygen transfer rate reduction. Yet, if relatively large quantities of antifoam are added, the gas holdup and the oxygen transfer rate may remain low during a long period of time, and it will take several hours, to enhance them to desirable values. Optimum amounts of antifoam agent additions depend upon variables such as microorganism, substrate, fermentation conditions, antifoaming type, differential pressure set point among others. Optimum amounts of antifoam agent additions and time span between additions shall be determined in advance in trial runs.

Figure 4:
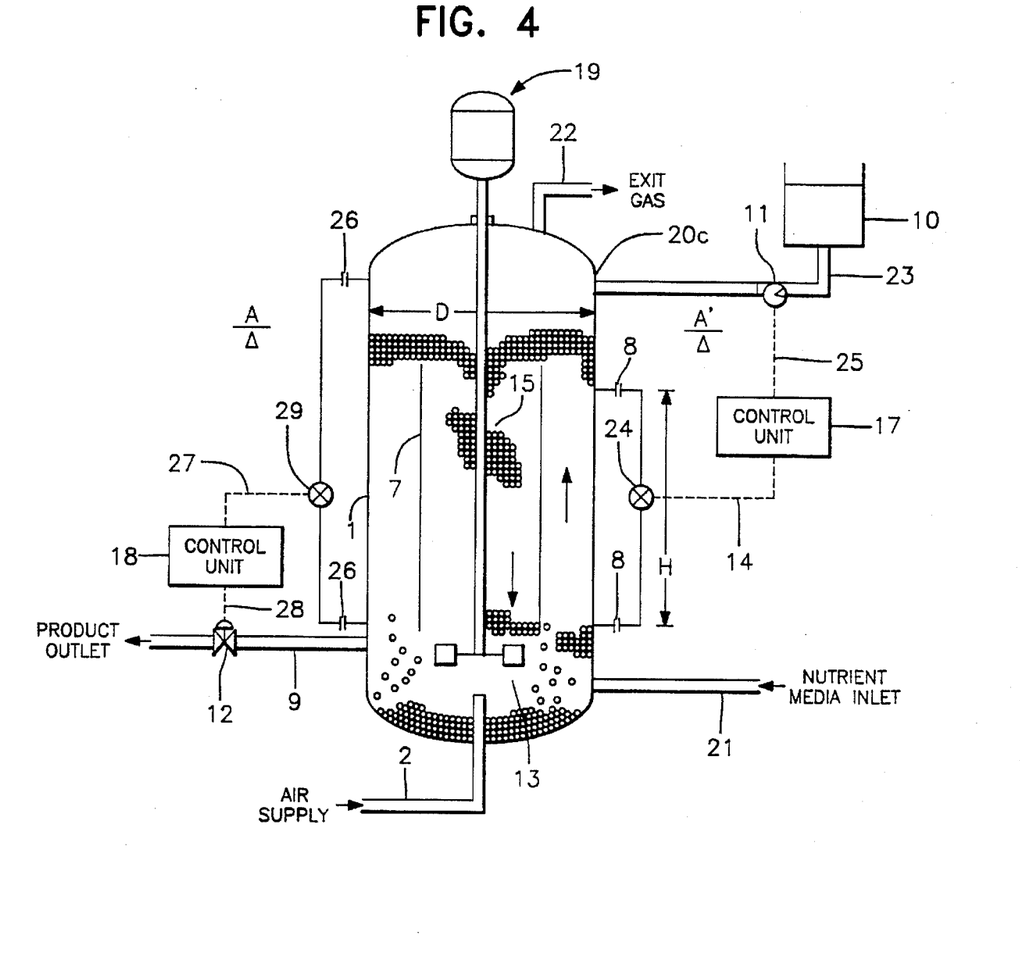
FIG. 4 is a side elevation of a fourth embodiment of the present invention.

FIG. 4 illustrates another form of the invention apparatus 20c. The elements of apparatus 20c have the same function as those similarly described above and having the same reference numerals. In particular the apparatus 20c differs in that instead of a Sonicator 10, as in FIG. 2, an output signal 25 from the control unit 17, provides an activating signal to adjust the flow rate of antifoam agent from supply 10, delivered to the fermentor through tube 23, by pump 11. The same control of antifoam delivery is similarly illustrated with reference to FIG. 3.

In apparatus 20, 20a, 20b and 20c described above, hydrodynamic foam suppression is achieved by maintaining a proper gassed broth level and by maintaining a proper broth level respectively. As it is well known in the art, other means can be employed to provide a suitable signal output in response to the gassed broth level or alternatively in response to the broth content, to provide a suitable signal for controlling any of these parameters.

Various applications for the fermentor and fermentation method of our invention are feasible for both production of microorganisms to obtain cellular protein or for production of various extracellular and intracellular products by biochemical conversion. Preferably yeast or bacteria are cultivated at temperatures between 20° to 45° C. under aerobic conditions, in the fermentor containing a broth with a pH value of 2.5 to 8. The fermentor 20 is especially useful for conducting continuous fermentation process, wherein a nutrient medium is continuously fed through at least an inlet 21 into the vessel 1, and a broth containing the desired microbial cells and metabolites is continuously withdrawn via the outlet 9 for further processing (not shown). Such further processing can include recovery of cells from the fermentation effluent by conventional means, such as centrifugation, filtration or other separation means. The cellular product can be washed to remove unconsumed mineral salts and extracellular products, such as amino acids, enzymes, biopolymers and the like. The washed cells can then be dried to produce a dried protein rich product. The washings and the substantially cell free effluent contain the residual mineral salts not incorporated into the cells and extracellular products. These streams can be treated to recover or isolate extracellular products such as enzymes, biopolymers, and others. For instance, a lower alcohol such as methanol or ethanol can be used to precipitate any polymeric material produced extracellularly by the microbial cells. The cell free effluent also can be treated by solvent extraction to recover other extracellular products. Alternatively, the total fermentation effluent can be dried to produce a dried product containing cells, salts, and other water soluble substances.

We claim:

1. In process for the production of microorganisms or their metabolites in a fermentor vessel having an upper region, a lower region and guiding means for providing at least one ascending flow chamber and at least one descending flow chamber, said chambers communicating at said upper and lower regions, wherein a gassed fermentation broth containing microorganisms, which are to be aerobically cultured, is continuously circulated, the improvement comprising:

a) providing gas holdup sensing means for sensing the gas holdup of said fermentation broth;

b) providing means, at least partially disposed within the fermentor, for releasing constituents of at least a portion of the microorganisms contained in said fermentor vessel;

c) inducing a liquid vortex in the upper region of the fermentor vessel by maintaining said gassed fermentation broth at a suitable level above said guiding means, said vortex thereby preventing the formation of a foam layer in the upper region of the fermentor vessel;

d) detecting gas holdup of said fermentation broth with said gas holdup sensing means; and e) controlling gas holdup by activating or alternatively, deactivating said means for releasing constituents of the microorganisms with a control means, which is operatively connected to said gas holdup sensing means, and whereby in operation the detected gas holdup is used by said control means to activate said release in response to a predetermined minimum gas holdup or alternatively, to deactivate the release of the constituents of said microorganisms, in response to a predetermined maximum gas holdup.

2. The process of claim 1 wherein said gassed fermentation broth level is maintained by withdrawing a portion of said gassed fermentation broth through an overflow pipe.

3. The process of claim 1 wherein said gassed fermentation broth level is maintained by withdrawing a portion of said gassed fermentation broth through a controlled outlet in response to an outlet signal of a controller.

4. The process of claim 3 further comprising providing an interface sensing device operatively connected to said controller and measuring the interface between the gassed fermentation broth and gas phase in said fermentor vessel with said interface sensing device.

5. The process of claim 3 further comprising providing, a differential pressure sensing device operatively connected to said controller and measuring said gassed broth level in said fermentor vessel with said differential pressure sensing device.

6. The process of claim 1 wherein detecting gas holdup comprises measuring a pressure difference in said gassed fermentation broth.

7. The process of claim 1 wherein detecting gas holdup comprises measuring refractive index of said gassed fermentation broth in said fermentor.

8. The process of claim 1 wherein detecting gas holdup comprises measuring electric conductivity of said gassed fermentation broth in said fermentor.

9. The process of claim 1 wherein detecting gas holdup comprises measuring heat conductivity of said gassed fermentation broth in said fermentor.

10. In an apparatus for production of microorganisms or their metabolites comprising a closed fermentor vessel for holding a gassed fermentation broth, said vessel having an upper region, a lower region and guiding means for providing at least an ascending flow chamber and at least one descending flow chamber, said chambers communicating at said lower region and said upper region, a first inlet for introducing a liquid into said vessel, a second inlet for introducing a gas into said vessel, means for dispersing said gas into said liquid within said fermentor vessel and producing a gassed fermentation broth, a gas outlet located in the upper region of said fermentor vessel, a liquid outlet for withdrawing a portion of the liquid from said fermentor vessel and means at least partially disposed within said fermentor vessel for causing the release of constituents of at least a portion of the microorganisms within said fermentor vessel, the improvement comprising:

(1) means for preventing the formation of a foam layer in an upper region of the vessel comprising means for maintaining said gassed fermentation broth at a predetermined level, such that in use said broth is maintained at a predetermined level above the guiding means within the fermentor vessel and a vortex is induced as a result of gassed fermentation broth flow deflection from the ascending flow chamber into the descending flow chamber in the upper region of said fermentor vessel;

(2) gas holdup sensing means at least partially disposed within said fermentation vessel for providing an output signal responsive to sensed gas holdup of said gassed fermentation broth; and (3) control means, operatively connected to said gas holdup sensing means and to said means for releasing constituents of the microorganisms, wherein said control means controls the release of constituents of a portion of said microorganisms in response to said output signal of said gas holdup sensing means.

11. The apparatus of claim 10 wherein said means for maintaining the gassed fermentation broth level comprises at least an overflow pipe.

12. The apparatus of claim 10 wherein said means for maintaining the gassed fermentation broth level comprises an outlet operatively connected to a second control means and to an interface sensing device which detects the fermentation broth level by measuring the interface between the gassed fermentation broth and gas phase in said fermentor vessel, such that in use said broth is withdrawn from said fermentor vessel through said outlet, in response to a signal received from said control means in response to the level detected with the interface sensing device.

13. The apparatus of claim 10 wherein said means for maintaining the fermentation broth level comprises an outlet operatively connected to a second control means and to a differential pressure sensing device which measures the level of said broth in said fermentor vessel, such that in use said fermentation broth is withdrawn from said fermentor vessel through said outlet, in response to a signal received from said control means which is responsive to the level measured with the differential pressure sensing device.

14. The apparatus of claim 10 wherein said gas holdup sensing means comprises at least one differential pressure sensing device.

15. The apparatus of claim 10 wherein said gas holdup sensing means comprises a refractive index measuring device.

16. The apparatus of claim 10 wherein said gas holdup sensing means comprises an electric conductivity measuring device.

17. The apparatus of claim 10 wherein said gas holdup sensing means comprises a heat conductivity measuring device.

* * * * *